United States Patent
Kuwayama

(10) Patent No.: US 11,205,263 B2
(45) Date of Patent: Dec. 21, 2021

(54) REMOTE IMAGE INTERPRETATION MANAGEMENT APPARATUS, REMOTE IMAGE INTERPRETATION SYSTEM AND STORAGE MEDIUM

(71) Applicant: KONICA MINOLTA, INC., Chiyoda-ku (JP)

(72) Inventor: Naokazu Kuwayama, Chiyoda-ku (JP)

(73) Assignee: Konica Minolta, Inc., Tokyo (JP)

( * ) Notice: Subject to any disclaimer, the term of this patent is extended or adjusted under 35 U.S.C. 154(b) by 74 days.

(21) Appl. No.: 16/415,092

(22) Filed: May 17, 2019

(65) Prior Publication Data

US 2019/0370962 A1 Dec. 5, 2019

(30) Foreign Application Priority Data

Jun. 4, 2018 (JP) .............................. JP2018-106575

(51) Int. Cl.
  *G06T 7/00* (2017.01)
  *G06K 9/42* (2006.01)
  *G06K 9/46* (2006.01)

(52) U.S. Cl.
  CPC .............. *G06T 7/0012* (2013.01); *G06K 9/42* (2013.01); *G06K 9/4609* (2013.01)

(58) Field of Classification Search
  CPC ........ G16H 30/20; G06T 7/0012; G06K 9/42; G06K 9/4609
  See application file for complete search history.

(56) References Cited

U.S. PATENT DOCUMENTS 8,103,524 B1 * 1/2012 Rogers .................. G16H 70/00
  705/2
8,150,750 B2 * 4/2012 Ray ........................ G06Q 10/10
  705/35

(Continued)

FOREIGN PATENT DOCUMENTS

JP      2004013268 A *  1/2004
JP      4962984          4/2012

(Continued)

OTHER PUBLICATIONS

Tabatabaee et al. "Investigation of outliers of evaluation scores among school of health instructors using outlier-determination indices." Journal of Advances in Medical Education & Professionalism 4.1 (2016): 21. (Year: 2016).*

*Primary Examiner* — Katrina R Fujita
(74) *Attorney, Agent, or Firm* — Cozen O'Connor

(57) ABSTRACT

A remote image interpretation management apparatus includes a hardware processor. The hardware processor obtains, from a storage storing evaluation values about quality of image interpretation reports by evaluator and by image interpretation facility and/or image interpretation doctor, evaluation values of evaluators who have evaluated a predetermined number of image interpretation reports or more. Based on the obtained evaluation values of the evaluators, for each of the evaluators, the hardware processor calculates a statistic of the evaluation values of the evaluator and normalizes the evaluation values with the calculated statistic, thereby obtaining normalized evaluation values for the respective evaluators. For each image interpretation facility and/or each image interpretation doctor, the hardware processor calculates a mean value based on the normalized evaluation values of the respective evaluators.

6 Claims, 8 Drawing Sheets

(56) References Cited

U.S. PATENT DOCUMENTS

| | | | |
|---|---|---|---|
| 8,533,194 B1* | 9/2013 | Ravid | G06N 20/00 |
| | | | 707/737 |
| 8,554,601 B1* | 10/2013 | Marsh | G06Q 30/0278 |
| | | | 705/7.32 |
| 8,805,844 B2* | 8/2014 | Schorzman | G06F 16/9535 |
| | | | 707/738 |
| 2007/0288264 A1* | 12/2007 | Brown | G06Q 50/22 |
| | | | 705/2 |
| 2008/0103816 A1* | 5/2008 | Kaplan | G16H 40/20 |
| | | | 705/2 |
| 2009/0259488 A1* | 10/2009 | Gounares | G06Q 10/06398 |
| | | | 705/3 |
| 2010/0114744 A1* | 5/2010 | Gonen | G06Q 40/06 |
| | | | 705/35 |
| 2010/0235295 A1* | 9/2010 | Zides | G06Q 30/0282 |
| | | | 705/347 |
| 2013/0282427 A1* | 10/2013 | Dvorak | G06Q 50/01 |
| | | | 705/7.29 |
| 2015/0310508 A1* | 10/2015 | Pattekar | G06Q 30/0282 |
| | | | 705/2 |
| 2015/0347694 A1* | 12/2015 | Chung | G16H 30/20 |
| | | | 705/3 |
| 2018/0293663 A1* | 10/2018 | Spiegel | G16H 10/60 |

FOREIGN PATENT DOCUMENTS

| | | | | |
|---|---|---|---|---|
| JP | 5266975 B2 * | 8/2013 | | |
| JP | 6017841 B2 * | 11/2016 | | G06Q 30/02 |
| JP | 2017021641 A * | 1/2017 | | |

* cited by examiner

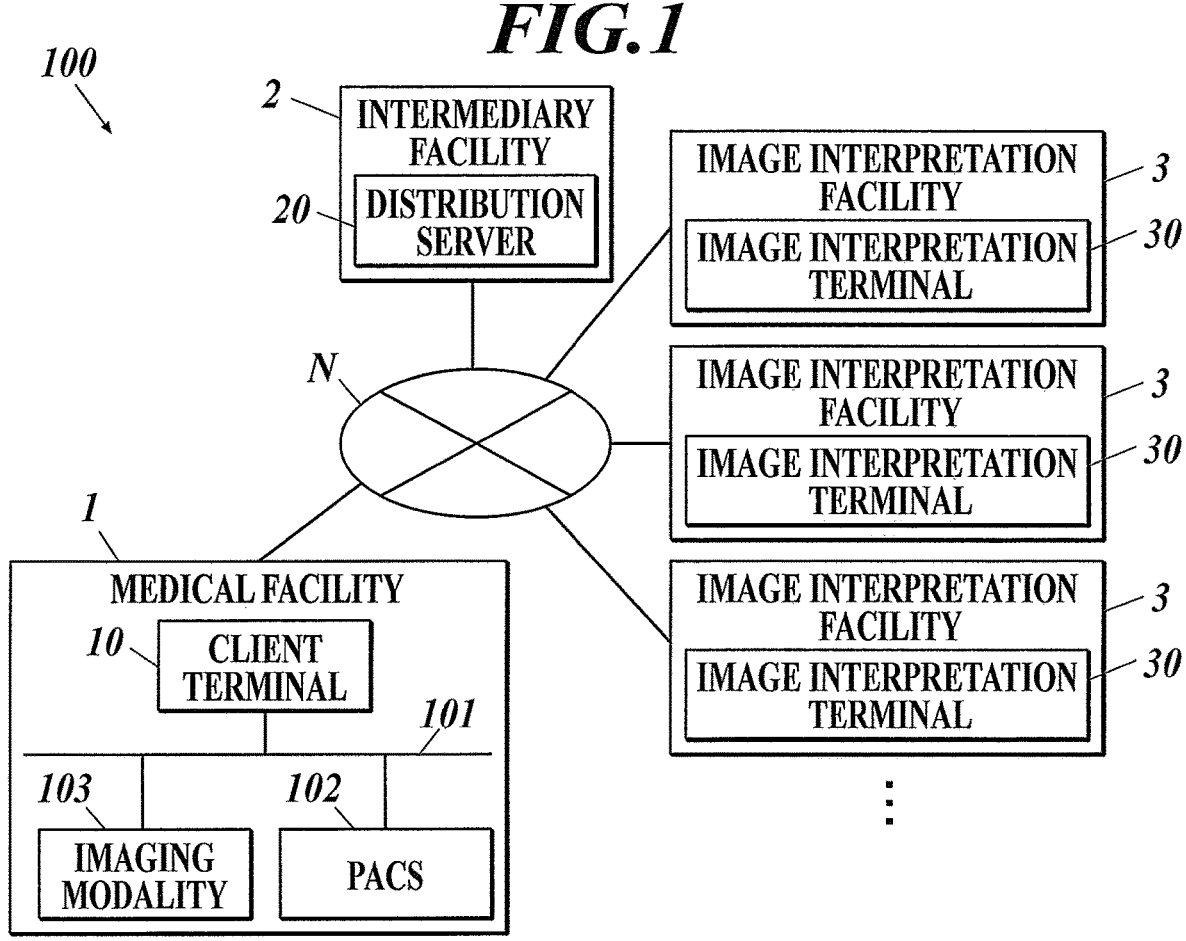
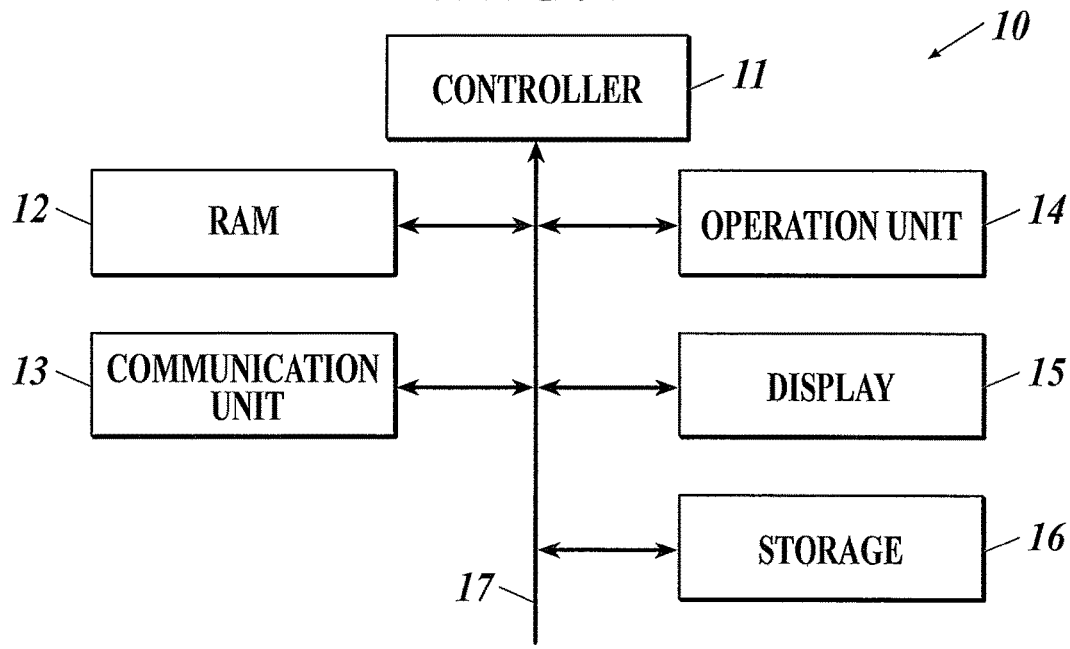

REMOTE IMAGE INTERPRETATION MANAGEMENT APPARATUS, REMOTE IMAGE INTERPRETATION SYSTEM AND STORAGE MEDIUM

BACKGROUND

1. Technological Field

This invention relates to a remote image interpretation management apparatus, a remote image interpretation system, and a storage medium.

2. Description of the Related Art

In recent years, there have been known remote image interpretation systems by which medical images taken at medical facilities are interpreted by image interpretation companies which consist of image interpretation specialists and are located at remote places, and the diagnoses (interpretation results) are provided to the medical facilities. Such remote image interpretation services contribute to the improvement of diagnostic accuracy and treatment efficiency by swiftly providing precise diagnoses to medical facilities which have no image interpretation doctors.

A typical remote image interpretation system includes an organization which intermediates between medical facilities and image interpretation companies. A server in such an intermediary facility connects to terminals in medical facilities and terminals in image interpretation companies via a communication network, such as the Internet, to communicate data, and the medical facilities send medical images to the image interpretation companies via the intermediary facility, and the image interpretation companies send prepared image interpretation reports to the medical facilities via the intermediary facility.

Usually, an intermediary facility assigns requests for image interpretation to image interpretation companies and/or image interpretation doctors without allowing clients, namely medical facilities, to name an image interpretation company(ies) or an image interpretation doctor(s). Image interpretation companies need to provide image interpretation reports swiftly. There are cases where a client is dissatisfied with the quality of an image interpretation report provided by an image interpretation company owing to absence of skilled image interpretation doctors in the image interpretation company at the time of receipt of the request. Because such internal situation is not normally disclosed to clients, the clients find it difficult to estimate the level of quality of image interpretation reports that each image interpretation company maintains in preparation of image interpretation reports.

In view of such circumstances, it is desirable to allow clients to name an image interpretation company(ies) or an image interpretation doctor(s) on the basis of quality evaluation results which have been given to image interpretation reports.

In relation to this, on the Internet, there are evaluation websites where users evaluate movies, services and dishes at restaurants, or the like, and results calculated on the basis of accumulated evaluation values are displayed. However, each website may use a different evaluation standard, such as three-scale evaluation with three levels of evaluation criteria or five-scale evaluation with five levels of evaluation criteria, and evaluate the same evaluation object therewith. Japanese Patent No. 4962984 discloses a technology to make such evaluation criteria, which are different from website to website, uniform, thereby converting evaluation values into those which are comparable to one another.

The evaluation standard also varies from evaluator to evaluator. Meaning of an evaluation value about an evaluation object differs, for example, depending on whether the evaluator often gives high evaluations or low evaluations. Furthermore, the evaluation standard of evaluators who rarely make evaluations tends to vary compared to that of evaluators who often make evaluations. Furthermore, evaluation results may be arbitrarily-manipulated evaluation results. Variation in the evaluation standard between evaluators should be reduced as much as possible to calculate a reliable result(s) on the basis of reliable evaluation values.

SUMMARY

The present invention has been conceived in view of such problems. Objects of the present invention include providing a remote image interpretation management apparatus, a remote image interpretation system, and a storage medium which provide high-quality remote interpretation services by allowing clients to name request destinations on the basis of reliable evaluation values.

In order to achieve at least one of the abovementioned objects, according to a first aspect of the present invention, there is provided a remote image interpretation management apparatus including a hardware processor which: obtains, from a storage storing evaluation values about quality of image interpretation reports by evaluator and by image interpretation facility and/or image interpretation doctor, evaluation values of evaluators who have evaluated a predetermined number of image interpretation reports or more; based on the obtained evaluation values of the evaluators, for each of the evaluators, calculates a statistic of the evaluation values of the evaluator and normalizes the evaluation values with the calculated statistic, thereby obtaining normalized evaluation values for the respective evaluators; and for each image interpretation facility or each image interpretation doctor, calculates a mean value based on the normalized evaluation values of the respective evaluators.

According to a second aspect of the present invention, there is provided a remote image interpretation system including: a client terminal which makes a request for interpretation of a medical image; an image interpretation terminal which interprets a medical image; and a remote image interpretation management apparatus which relays the request made by the client terminal to the image interpretation terminal, wherein the remote image interpretation management apparatus includes a hardware processor which: obtains, from a storage storing evaluation values about quality of image interpretation reports by evaluator and by image interpretation facility and/or image interpretation doctor, evaluation values of evaluators who have evaluated a predetermined number of image interpretation reports or more; based on the obtained evaluation values of the evaluators, for each of the evaluators, calculates a statistic of the evaluation values of the evaluator and normalizes the evaluation values with the calculated statistic, thereby obtaining normalized evaluation values for the respective evaluators; and for each image interpretation facility or each image interpretation doctor, calculates a mean value based on the normalized evaluation values of the respective evaluators.

According to a third aspect of the present invention, there is provided a non-transitory computer readable storage medium storing a program to cause a computer of a remote image interpretation management apparatus which relays a request for image interpretation made by a medical facility to an image interpretation facility to: obtain, from a storage storing evaluation values about quality of image interpretation reports by evaluator and by image interpretation facility and/or image interpretation doctor, evaluation values of evaluators who have evaluated a predetermined number of image interpretation reports or more; based on the obtained evaluation values of the evaluators, for each of the evaluators, calculate a statistic of the evaluation values of the evaluator and normalize the evaluation values with the calculated statistic, thereby obtaining normalized evaluation values for the respective evaluators; and for each image interpretation facility or each image interpretation doctor, calculate a mean value based on the normalized evaluation values of the respective evaluators.

BRIEF DESCRIPTION OF THE DRAWINGS

The advantages and features provided by one or more embodiments of the present invention will become more fully understood from the detailed description given hereinbelow and the appended drawings which are given by way of illustration only, and thus are not intended as a definition of the limits of the present invention, wherein:

FIG. 1 shows a schematic configuration of a remote image interpretation system according to an embodiment(s);

FIG. 2 shows a functional configuration of a client terminal;

DETAILED DESCRIPTION OF EMBODIMENTS

Figure 3:
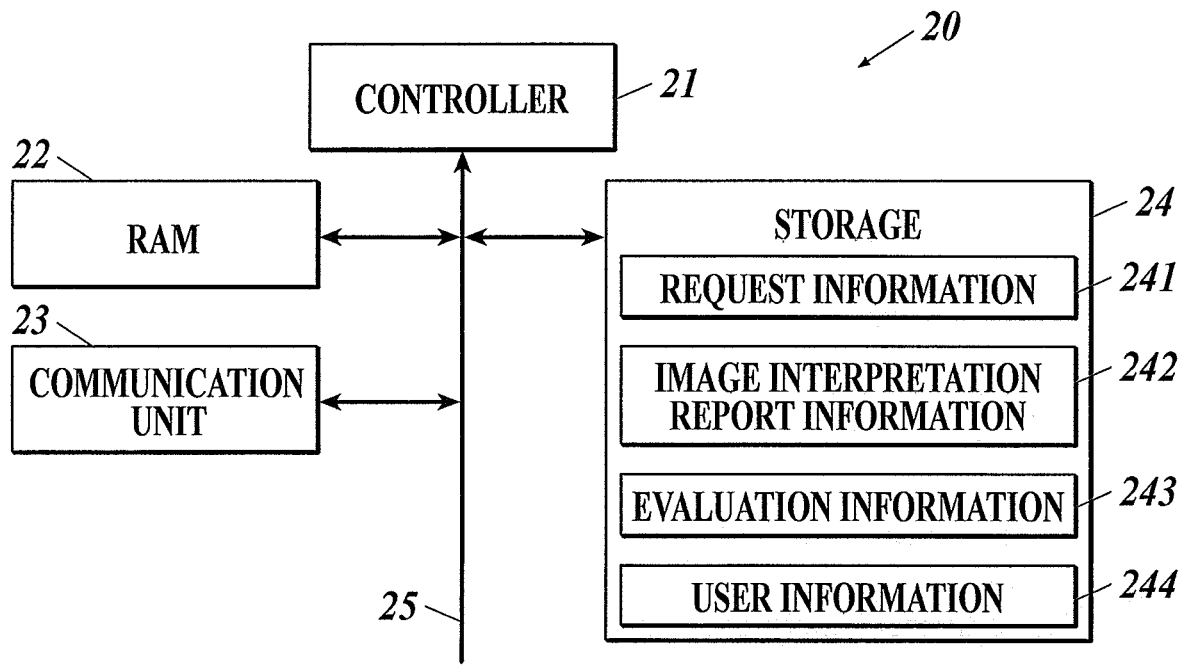
FIG. 3 shows a functional configuration of a distribution server.

Hereinafter, one or more embodiments of a remote image interpretation system of the present invention will be described with reference to the drawings. However, the scope of the present invention is not limited to the disclosed embodiments.

FIG. 1 shows a configuration of a remote image interpretation system 100 according to an embodiment(s).

As shown in FIG. 1, this remote image interpretation system 100 allows a medical facility (or facilities) 1 and image interpretation facilities (or facility) 3 to cooperate with one another via an intermediary facility 2.

Examples of the medical facility 1 include a general hospital, a special hospital, a medical examination facility, and a privately-managed or small-sized clinic.

The intermediary facility 2 is an organization which cooperates with a plurality of image interpretation facilities 3, and serves as an agency to provide remote image interpretation services of the image interpretation facilities 3 to the medical facility 1.

Each image interpretation facility 3 is an organization consisting of image interpretation doctors, such as radiologist, and specializing in image interpretation, and at a remote place, interprets medical images including X-ray images, MRI images, and CT images sent from the medical facility 1, and sends image interpretation reports as diagnoses (interpretation results) to the medical facility 1.

As shown in FIG. 1, in the remote image interpretation system 100, a client terminal(s) 10 installed in the medical facility 1, an image interpretation request distribution server (hereinafter simply "distribution server") 20 installed in the intermediary facility 2, and image interpretation terminals 30 installed in the image interpretation facilities 3 connect to one another to communicate data via a communication network N, such as the Internet.

The number of medical facilities 1 and the number of image interpretation facilities 3 which constitute the remote image interpretation system 100 are not particularly limited. In this embodiment, one distribution server 20 connects to one client terminal 10 and a plurality of image interpretation terminals 30, and one intermediary facility 2 cooperates with one medical facility 1 and a plurality of image interpretation facilities 3.

The number of client terminals 10 in each medical facility 1 and the number of image interpretation terminals 30 in each image interpretation facility 3 are not particularly limited. Each facility may have two or more terminals.

The client terminal 10 is a computer used in the medical facility 1 to request remote image interpretation from the image interpretation facilities 3 and to receive image interpretation reports from the image interpretation facilities 3 via the intermediary facility 2. The client terminal 10 is also used to evaluate, via the intermediary facility 2, the image interpretation facilities 3 and/or image interpretation doctors that have prepared (created) image interpretation reports.

Specifically, to request image interpretation, the client terminal 10 accesses the distribution server 20 via the communication network N, and sends request information to the distribution server 20, and to refer to an image interpretation report, the client terminal 10 accesses the distribution server 20 via the communication network N, and receives image interpretation report information managed by the distribution server 20. Also, to input an evaluation, the client terminal 10 accesses the distribution server 20 via the communication network N, and sends evaluation information on an image interpretation doctor and/or an image interpretation facility 3 to the distribution server 20.

The client terminal 10 connects to a PACS (Picture Archiving and Communication System) 102 installed in the medical facility 1 to communicate data via an in-house network 101, such as a LAN (Local Area Network), and retrieves medical information from the PACS 102.

The PACS 102 is an in-house server, and stores the medical information, such as image data of medical images generated by an in-house imaging modality 103, associated with patient information and/or examination information.

Examples of the imaging modality 103 include various medical imaging apparatuses which generate images related to examination results, such as X-ray radiography apparatuses including a CR (Computed Radiography) apparatus and an FPD (Flat Panel Detector), an ultrasound apparatus, an endoscopic apparatus, a CT (Computed Tomography) apparatus, and an MRI (Magnetic Resonance Imaging) apparatus.

FIG. 2 shows a hardware configuration of the client terminal 10.

As shown in FIG. 2, the client terminal 10 includes a controller 11, a RAM 12, a communication unit 13, an operation unit 14, a display 15, and a storage 16. These components connect to one another via a bus 17.

The controller 11 includes a CPU, and integrally controls operations of the components of the client terminal 10. The controller 11 reads out various programs stored in the storage 16 and loads them into the RAM 12 to perform various processes in cooperation with the programs.

The RAM 12 forms a work area to temporarily store programs, input/output data, parameters and so forth read out from the storage 16 in various processes which are performed and controlled by the controller 11.

The communication unit 13 includes a network interface, and sends and receives data to and from external apparatuses connected via the communication network N or the in-house network 101. Specifically, the communication unit 13 sends evaluation results, request information to request remote image interpretation and so forth set with the operation unit 14 to the distribution server 20.

The operation unit 14 includes: a keyboard equipped with cursor keys, numeric keys, and various function keys; and a pointing device, such as a mouse. The operation unit 14 outputs, to the controller 11, operation signals input by key operations to the keyboard or by mouse operations.

The display 15 includes a monitor, such as an LCD, and displays various screens in accordance with instructions of display signals input from the controller 11.

The storage 16 includes an HDD (Hard Disk Drive) and/or a nonvolatile semiconductor memory. The storage 16 stores various programs which are executed by the controller 11, and also stores parameters and data which are required for execution of the programs.

The distribution server 20 functions as a remote image interpretation management apparatus. Specifically, the distribution server 20 accumulates and manages the request information received from the client terminal 10, and sends the request information to an image interpretation facility(ies) 3 named by a user(s) of the client terminal 10. Furthermore, the distribution server 20 accumulates and manages the image interpretation report information received from the image interpretation facilities 3, and provides the image interpretation report information to the client terminal 10 as requested. Furthermore, the distribution server 20 manages the following as evaluation information: evaluation value information on each image interpretation facility 3 or each image interpretation doctor received from the client terminal 10; and mean evaluation value information obtained from accumulated evaluation values.

FIG. 3 shows a hardware configuration of the distribution server 20.

As shown in FIG. 3, the distribution server 20 includes a controller 21, a RAM 22, a communication unit 23, and a storage 24. These components connect to one another via a bus 25.

The controller 21 includes a CPU, and integrally controls operations of the components of the distribution server 20. The controller 21 reads out various programs stored in the storage 24 and loads them into the RAM 22 to perform various processes in cooperation with the programs.

The RAM 22 forms a work area to temporarily store programs, input/output data, parameters and so forth read out from the storage 24 in various processes which are performed and controlled by the controller 21.

The communication unit 23 includes a network interface, and sends and receives data to and from external apparatuses connected via the communication network N. For example, the communication unit 23 receives the request information to request remote image interpretation sent from the client terminal 10, and sends the information to the image interpretation terminal(s) 30. The communication unit 23 also receives the image interpretation report information sent from the image interpretation terminal(s) 30, and sends the information to the client terminal 10.

The storage 24 includes an HDD and/or a nonvolatile semiconductor memory. The storage 24 stores various programs which are executed by the controller 21, and also stores parameters and data which are required for execution of the programs. The storage 24 also stores request information 241, image interpretation report information 242, evaluation information 243, and user information 244.

The request information 241 is information sent from the client terminal 10 to the distribution server 20, the information including: information each specifying an image interpretation facility 3 or an image interpretation doctor; data of a medical image(s) to be interpreted; and information required for the image interpretation, such as imaging conditions and patient information.

The image interpretation report information 242 is information including an image interpretation report(s) each associated with identifying information. The image interpretation report(s) is a diagnosis prepared by an image interpretation doctor and sent from an image interpretation terminal 30 to the distribution server 20, and also is an image diagnosis report prepared by the image interpretation doctor and describing all the indications on which the diagnosis is based. The image interpretation report information 242 is information including such an image interpretation report(s) each associated with (i) preparer identifying information which identifies an image interpretation facility 3 or an image interpretation doctor that has prepared the report and (ii) requester identifying information which identifies the medical facility 1 or a user belonging to the medical facility 1 that has requested preparation of the report.

The evaluation information 243 is information indicating an evaluation result(s) about an image interpretation facility(ies) 3 and/or an image interpretation doctor(s) by a user(s) belonging to the medical facility 1. The evaluation information 243 includes: evaluation value information including an evaluation value(s) about an image interpretation facility(ies) 3 or an image interpretation doctor(s), the evaluation value(s) each being associated with evaluator identifying information which identifies an evaluator who has made the evaluation; and mean evaluation value information obtained by the distribution server 20 performing calculation based on the evaluation value information (accumulated evaluation values).

The user information 244 is information for managing a user(s) of the client terminal(s) 10 in the medical facility 1 and users of the image interpretation terminals 30 in the image interpretation facilities 3, the facilities 1 and 3 cooperating with the intermediary facility 2. The user information 244 stores, for each user (medical practitioner) of the client terminal 10, user ID, password, name, where the user belongs (medical facility, department), e-mail address, and so forth; and for each user (image interpretation doctor) of the image interpretation terminal 30, user ID, password, name, where the user belongs (image interpretation facility), e-mail address, and so forth.

Each image interpretation terminal 30 is a computer used in each image interpretation facility 3 to receive the request information from the medical facility 1 and to send image interpretation reports to the medical facility 1 via the intermediary facility 2.

Specifically, the image interpretation terminal 30 accesses the distribution server 20 via the communication network N, and receives the request information managed by the distribution server 20, and sends image interpretation reports to the distribution server 20.

Figure 4:
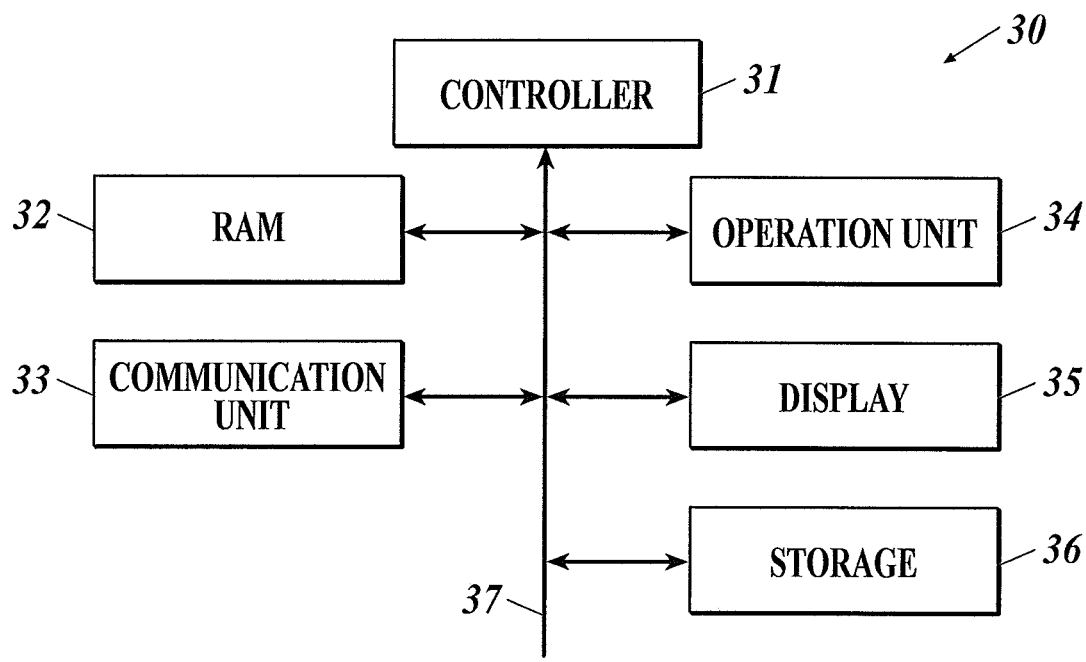
FIG. 4 shows a functional configuration of an image interpretation terminal.

FIG. 4 shows a hardware configuration of the image interpretation terminal 30.

As shown in FIG. 4, the image interpretation terminal 30 includes a controller 31, a RAM 32, a communication unit 33, an operation unit 34, a display 35, and a storage 36. These components connect to one another via a bus 37.

The controller 31 includes a CPU, and integrally controls operations of the components of the image interpretation terminal 30. The controller 31 reads out various programs stored in the storage 36 and loads them into the RAM 32 to perform various processes in cooperation with the programs.

The RAM 32 forms a work area to temporarily store programs, input/output data, parameters and so forth read out from the storage 36 in various processes which are performed and controlled by the controller 31.

The communication unit 33 includes a network interface, and sends and receives data to and from external apparatuses connected via the communication network N. Specifically, the communication unit 33 sends image interpretation reports set with the operation unit 34 to the distribution server 20.

The operation unit 34 includes: a keyboard equipped with cursor keys, numeric keys, and various function keys; and a pointing device, such as a mouse. The operation unit 34 outputs, to the controller 31, operation signals input by key operations to the keyboard or by mouse operations.

The display 35 includes a monitor, such as an LCD, and displays various screens in accordance with instructions of display signals input from the controller 31.

The storage 36 includes an HDD and/or a nonvolatile semiconductor memory. The storage 36 stores various programs which are executed by the controller 31, and also stores parameters and data which are required for execution of the programs.

[Evaluation Input Process]

Next, an evaluation input process of the remote image interpretation system 100 according to this embodiment is described. In the evaluation input process, a user who belongs to the medical facility 1 and has received an image interpretation report evaluates the quality of the image interpretation report, and thereby evaluates, as an evaluation object(s), an image interpretation facility 3 and/or an image interpretation doctor that have/has performed image interpretation.

Figure 5:
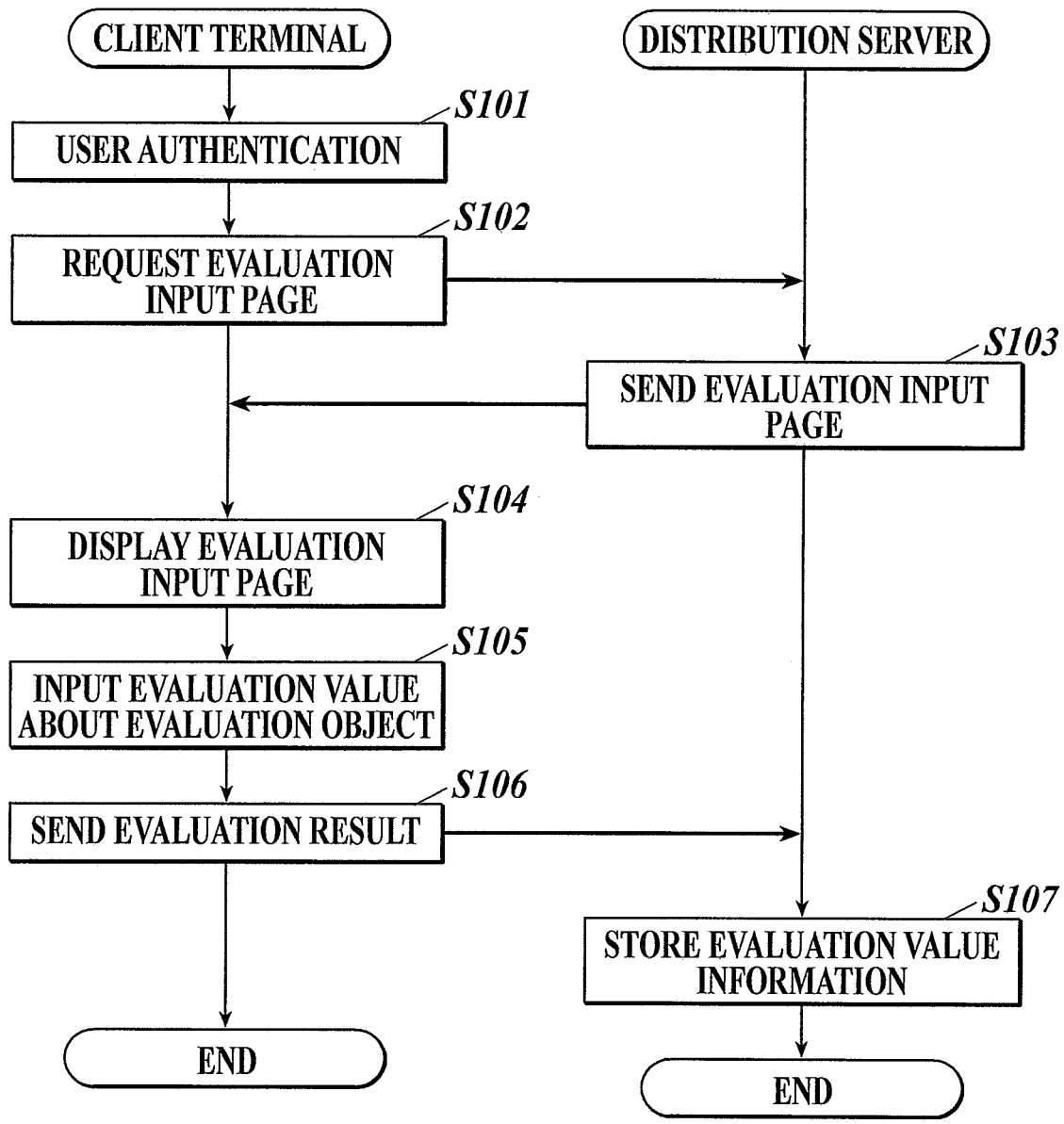
FIG. 5 is a flowchart showing an evaluation input process.

FIG. 5 is a flowchart showing the evaluation input process performed by the client terminal 10 and the distribution server 20.

First, a user of the client terminal 10 in the medical facility 1 is subjected to user authentication (Step S101). As an example of the user authentication, the user inputs his/her ID and password with the operation unit 14, and the distribution server 20 identifies the user by referring to the user information 244.

Next, the user of the client terminal 10 in the medical facility 1 requests an evaluation input page from the distribution server 20 of the intermediary facility 2 (Step S102). Specifically, the user of the client terminal 10 sends a request for an evaluation input page to the distribution server 20 via the communication unit 13 by manipulating a screen displayed on the display 15 with the operation unit 14.

When receiving the request for the evaluation input page, the distribution server 20 sends data for forming the evaluation input page to the client terminal 10 via the communication unit 23 (Step S103).

When receiving the data via the communication unit 13, the client terminal 10 forms the evaluation input page on the basis of the data, and displays the evaluation input page on the display 15 (Step S104).

The evaluation input page is a screen for the user of the client terminal 10 to input an evaluation(s) about an evaluation object(s) by operating the operation unit 14.

The user of the client terminal 10 refers to the evaluation input page displayed on the display 15, and inputs thereinto an evaluation value(s) about an evaluation object(s) by operating the operation unit 14 (Step S105).

The evaluation object(s) is/are an image interpretation facility 3 and/or an image interpretation doctor that have/has prepared an image interpretation report which the user who belongs to the medical facility 1 has received. The user who belongs to the medical facility 1 evaluates the image interpretation facility 3 or the image interpretation doctor on the basis of the quality of the image interpretation report, and inputs an evaluation value on a scale of zero to five. Here, as an example, the user of the client terminal 10 inputs an evaluation value(s) about the image interpretation facility 3 and the image interpretation doctor each as an evaluation object.

After inputting the evaluation value, the user of the client terminal 10 sends the evaluation value about the image interpretation facility 3 and the image interpretation doctor to the distribution terminal 20 via the communication unit 13 by operating the operation unit 14 (Step S106). When receiving the evaluation result (evaluation value) via the communication unit 23, the distribution server 20 attaches an evaluator identifying number which identifies the evaluator (user of the client terminal 10) to the evaluation value, thereby generating evaluation value information, and stores the generated evaluation value information in the storage 24 as the evaluation information 243 (Step S107).

Then, the evaluation input process ends.

[Remote Image Interpretation Request Process]

Next, operation of the remote image interpretation system 100 in requesting remote image interpretation is described.

Figure 6:
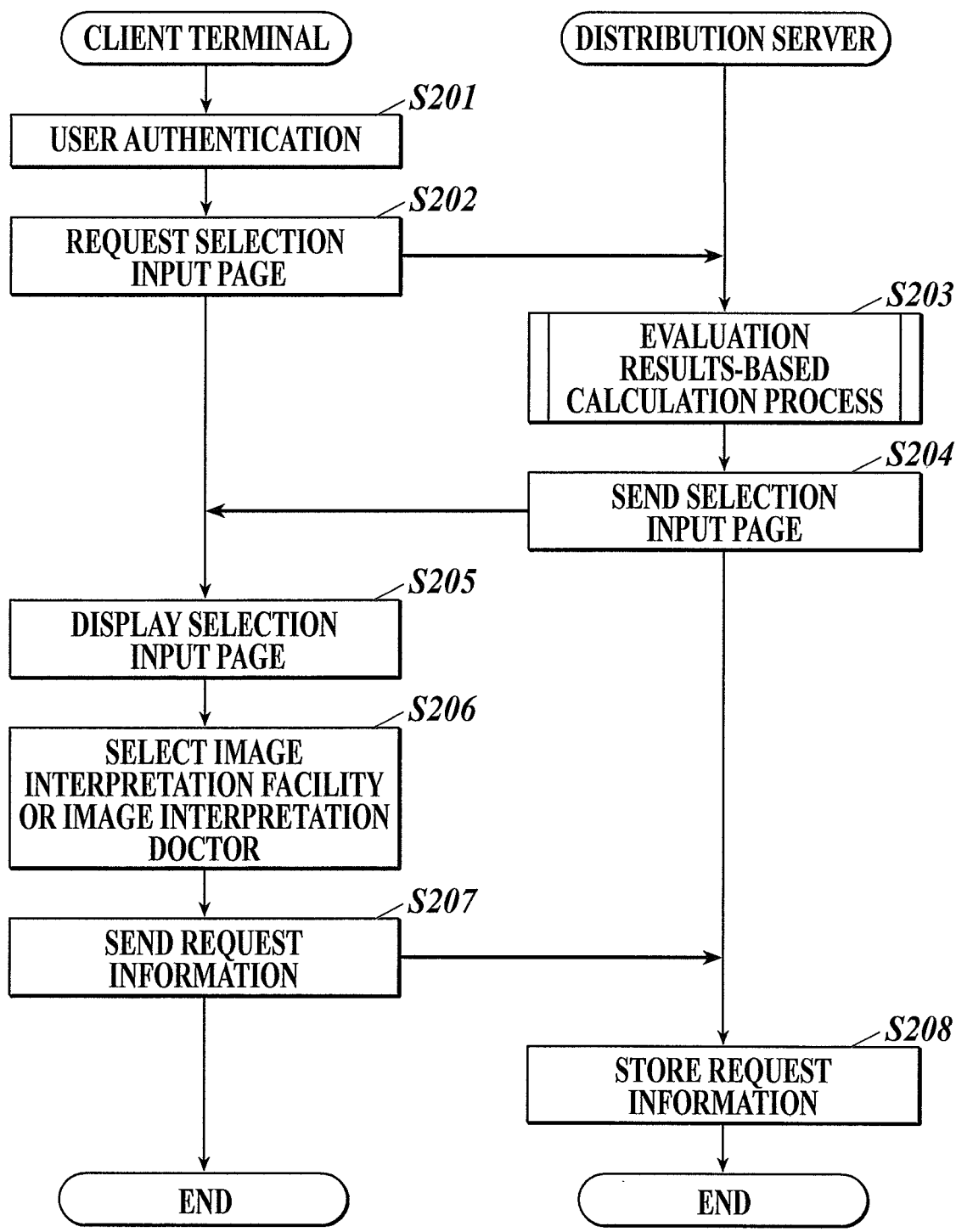
FIG. 6 is a flowchart showing a remote image interpretation request process.

FIG. 6 is a flowchart showing a remote image interpretation request process performed by the client terminal 10 and the distribution server 20.

First, a user of the client terminal 10 in the medical facility 1 is subjected to user authentication (Step S201). As an example of the user authentication, the user inputs his/her ID and password with the operation unit 14, and the distribution server 20 identifies the user by referring to the user information 244.

After being authenticated by the distribution server 20, the user of the client terminal 10 requests a selection input page from the distribution server 20 (Step S202). Specifically, the user of the client terminal 10 sends a request for a selection input page to the distribution server 20 via the communication unit 13 by manipulating a screen displayed on the display 15 with the operation unit 14.

The selection input page is a screen for the user of the client terminal 10 to select from the image interpretation facilities 3 cooperating with the intermediary facility 2 and/or image interpretation doctors belonging to the image interpretation facilities 3. With the selection input page displayed on the display 15, the user can request image interpretation from a desired image interpretation facility 3 or image interpretation doctor.

When receiving the request for the selection input page, the distribution server 20 performs an evaluation results-based calculation process (Step S203).

The evaluation results-based calculation process is a process of calculating statistics of evaluation values input in the evaluation input process (multiple times) by users of the client terminal(s) 10, and for each evaluation object, performing calculation based on the evaluation values (evaluation results) by using the statistics.

Figure 7:
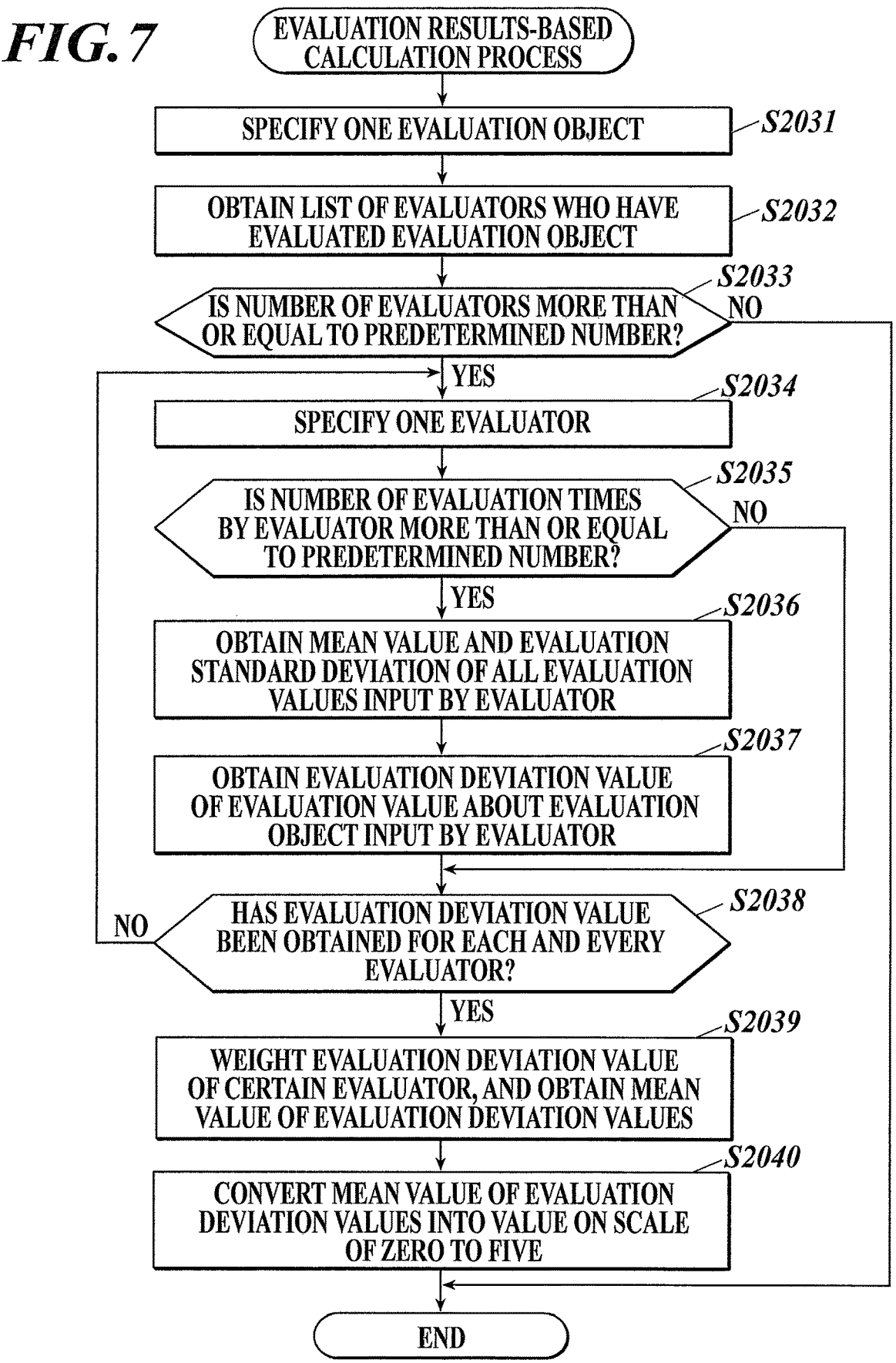
FIG. 7 is a flowchart showing operation of the distribution server in an evaluation results-based calculation process.

FIG. 7 is a flowchart showing operation of the distribution server 20 in the evaluation results-based calculation process. The evaluation results-based calculation process shown in FIG. 7 is performed by the controller 21 in cooperation with the program(s) stored in the storage 24.

First, the controller 21 specifies one evaluation object from the image interpretation facilities 3 and the image interpretation doctors (Step S2031). The following actions (steps) will be performed for this evaluation object.

Next, the controller 21 obtains a list of evaluators who have evaluated the evaluation object (Step S2032).

Specifically, the distribution server 20 refers to the evaluation value information stored as the evaluation information 243, extracts therefrom all the evaluators who have evaluated the evaluation object, and obtains the same as a list.

Next, the controller 21 determines whether or not the number of the evaluators is more than or equal to a predetermined number of evaluators (Step S2033). The predetermined number of evaluators (e.g. three evaluators) is a value considered to yield a reliable result (mean evaluation value) and is set beforehand. If the number of the evaluators who have evaluated the evaluation object is less than the predetermined number of evaluators, the controller 21 does not perform, for this evaluation object, the calculation based on the evaluation results.

When determining that the number of the evaluators is more than or equal to the predetermined number of evaluators (Step S2033: YES), the controller 21 proceeds to Step S2034. On the other hand, when determining that the number of the evaluators is less than the predetermined number of evaluators (Step S2033: NO), the controller 21 determines not to perform, for this evaluation object, the calculation based on the evaluation results, and ends the evaluation results-based calculation process (for this evaluation object).

At Step S2034, the controller 21 specifies one evaluator from the evaluators on the list. The following actions (steps) will be performed for this evaluator and repeated for each evaluator on the list.

Next, the controller 21 determines whether or not the number of evaluation times (the number of evaluations or the number of image interpretation reports evaluated) by the evaluator is more than or equal to a predetermined number of times (Step S2035).

The number of evaluation times is not the number of evaluation times that the evaluator has evaluated this evaluation object but the number of all the input times that the evaluator has input/made evaluations (the number of evaluation times that the evaluator has evaluated any evaluation object) which have been sent to the intermediary facility 2. The predetermined number of evaluation times (e.g. 10 times) is a value considered to yield a reliable result (mean evaluation value) and is set beforehand. Step S2035 aims to reduce variation in evaluation values by excluding, from the calculation based on the evaluation values, evaluations made by an evaluator(s) having the number of evaluation times less than the predetermined number of times on the basis of an idea that the evaluation standard of evaluators who rarely make evaluations tend to vary compared to that of evaluators who often make evaluations.

When determining that the number of evaluation times by the evaluator is more than or equal to the predetermined number of times (Step S2035: YES), the controller 21 proceeds to Step S2036. On the other hand, when determining that the number of evaluation times by the evaluator is less than the predetermined number of times (Step S2035: NO), the controller 21 proceeds to Step S2038.

At Step S2036, the controller 21 calculates statistics of all the evaluation values input by the evaluator.

The arithmetic mean $\mu$ of evaluations made n times (n evaluations) by the evaluator is expressed by the following formula (1), wherein $x_i$ represents an evaluation value (on a scale of zero to five being 0, 1, 2, 3, 4 and 5) input by the evaluator.

$$\mu = \frac{1}{n}\sum_{i=1}^{n} x_i \qquad (1)$$

The evaluation standard deviation G is expressed by the following formula (2).

$$\sigma = \sqrt{\frac{1}{n}\sum_{i=1}^{n}(x_i - \mu)^2} \qquad (2)$$

Next, the controller 21 obtains an evaluation deviation value(s) of the evaluation value(s) about the evaluation object input by the evaluator (Step S2037).

The evaluation deviation value is a value obtained by normalizing the evaluation value about the evaluation object input by the evaluator, using the statistics calculated from all the evaluation values input by the evaluator. Meaning of an evaluation value about an evaluation object differs depending on who the evaluator is because the evaluation standard varies from evaluator to evaluator (e.g. some evaluators often give high evaluations whereas others often give low evaluations). Hence, evaluation values about each evaluation object input by evaluators are normalized and thereby converted into evaluation deviation values which are comparable to one another.

The evaluation deviation value $T_i$ is calculated by normalizing the evaluation value with the following formula (3).

$$T_i = \alpha(x_i-\mu)/\sigma + 2.5 \qquad (3)$$

That is, on the assumption that the data of the evaluation values by the evaluator follows a normal distribution, if the data of the evaluation values are normalized such that the mean value becomes 2.5 and the standard deviation becomes a, the value of $T_i$ is obtained by the above formula (3).

For example, if it is desired that 10 percent of the evaluation values are 5, which is the highest among evaluation values of 0 to 5, $\alpha$=1.28 is obtained from the standard normal distribution table. By substituting 1.28 for $\alpha$ in the above formula (3), the evaluation deviation value $T_i$ is obtained.

After obtaining the evaluation deviation value $T_i$ for the evaluator, the controller 21 determines whether or not the evaluation deviation value has been obtained for each and every evaluator, who satisfies the condition at Step S2035 (Step S2038). When determining that the evaluation deviation value has not been obtained for each and every evaluator yet (Step S2038: NO), the controller 21 returns to Step S2034 and repeats the steps described above for the other evaluator(s).

On the other hand, when determining that the evaluation deviation value has been obtained for each and every evaluator (Step S2038: YES), the controller 21 proceeds to Step S2039.

At Step S2039, the controller 21 weights the evaluation deviation value(s) $T_i$ of a certain evaluator(s), and then obtains the mean value of the evaluation deviation values $T_i$.

A weight for each evaluator is predetermined according to his/her previous evaluation results, career and affiliation/membership (where he/she belongs). The evaluation deviation value(s) $T_i$ of a highly reliable evaluator(s), such as a distinguished doctor, may be weighted so as to be strongly reflected in the mean value. For example, the evaluation deviation value $T_i$ of such a reliable evaluator is multiplied (e.g. by 3), and the mean value is calculated in consistency with the multiplication (e.g. if there are other N evaluators, the mean value is calculated as the mean value of the evaluation deviation values $T_i$ of (1×3+N) evaluators).

After calculating the mean value of the evaluation deviation values as described above, the controller 21 converts the mean value into a value on a scale of zero to five (Step S2040), and ends the evaluation results-based calculation process. This process is repeated for another/other evaluation object(s) as needed.

After the evaluation results-based calculation process, referring back to FIG. 6, the distribution server 20 sends data for forming the selection input page reflecting the mean value of the evaluation deviation values (mean evaluation value) converted into the value on a scale of zero to five to the client terminal 10 via the communication unit 23 (Step S204). That is, the selection input page shows selectable image interpretation facilities 3 and image interpretation doctors along with their respective mean evaluation values.

When receiving the data via the communication unit 13, the client terminal 10 forms the selection input page on the basis of the received data, and displays the page on the display 15 (Step S205).

The user of the client terminal 10 refers to the mean evaluation values displayed on the selection input page, and selects an image interpretation facility 3 or an image interpretation doctor to request remote image interpretation by operating the operation unit 14 (Step S206).

Next, the client terminal 10 sends request information including the selection result at Step S206 and image data of a medical image(s) to be interpreted to the distribution server 20 (Step S207).

When receiving the request information, the distribution server 20 stores the information in the storage 24 as the request information 241 (Step S208). Then, the remote image interpretation request process ends.

[Image Interpretation Report Preparation Process]

Next, operation of the remote image interpretation system 100 in preparing an image interpretation report is described.

Figure 8:
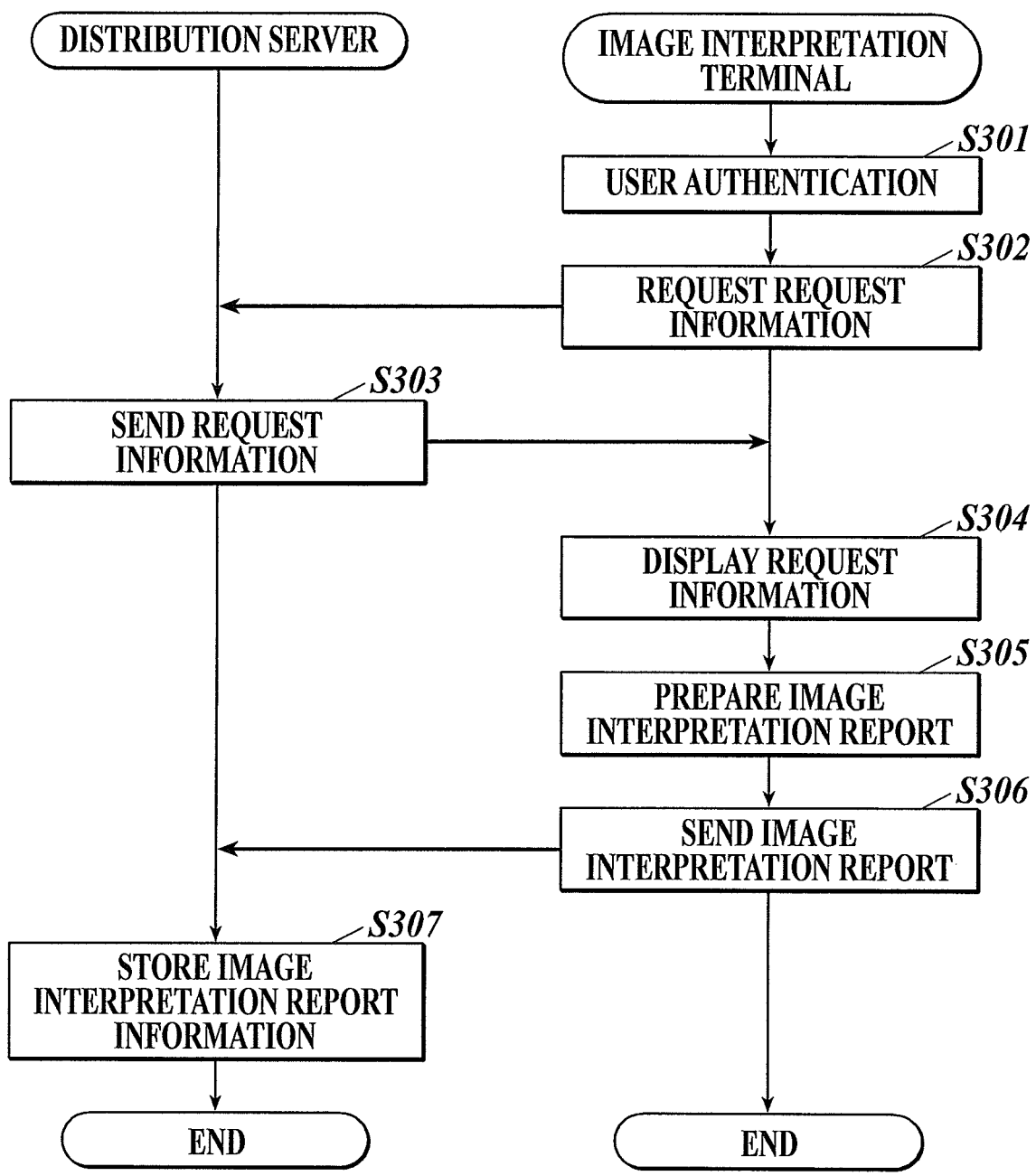
FIG. 8 is a flowchart showing an image interpretation report preparation process.

FIG. 8 is a flowchart showing an image interpretation report preparation process performed by the distribution server 20 and the image interpretation terminal(s) 30.

First, a user of the image interpretation terminal 30 in the image interpretation facility 3 is subjected to user authentication (Step S301). As an example of the user authentication, the user inputs his/her ID and password with the operation unit 34, and the distribution server 20 identifies the user by referring to the user information 244.

After being authenticated by the distribution server 20, the user of the image interpretation terminal 30 requests request information from the distribution server 20 (Step S302). Specifically, the user of the image interpretation terminal 30 sends a request for request information to the distribution server 20 via the communication unit 33 by manipulating a screen displayed on the display 35 with the operation unit 34.

When receiving the request for the request information, the distribution server 20 sends the request information 241 stored in the storage 24 to the image interpretation terminal 30 via the communication unit 23 (Step S303).

When receiving the request information via the communication unit 33, the image interpretation terminal 30 displays the request information on the display 35 (Step S304).

The user of the image interpretation terminal 30 refers to the request information, and checks if there is a request(s) for image interpretation to the user. If there is a request(s) for image interpretation to the user, the user downloads medical image data, displays the same on the display 35, and prepares an image interpretation report(s) (Step S305).

The image interpretation terminal 30 (attaches preparer identifying information to the prepared image interpretation report, and) sends the prepared image interpretation report to the distribution server 20 via the communication unit 33 (Step S306).

When receiving the image interpretation report, the distribution server 20 attaches a preparer identifying number to the image interpretation report, and stores the same in the storage 24 as the image interpretation report information 242 (Step S307). Then, the image interpretation report process ends.

[Image Interpretation Report Reference Process]

Next, operation of the remote image interpretation system 100 in referring to an image interpretation report is described.

Figure 9:
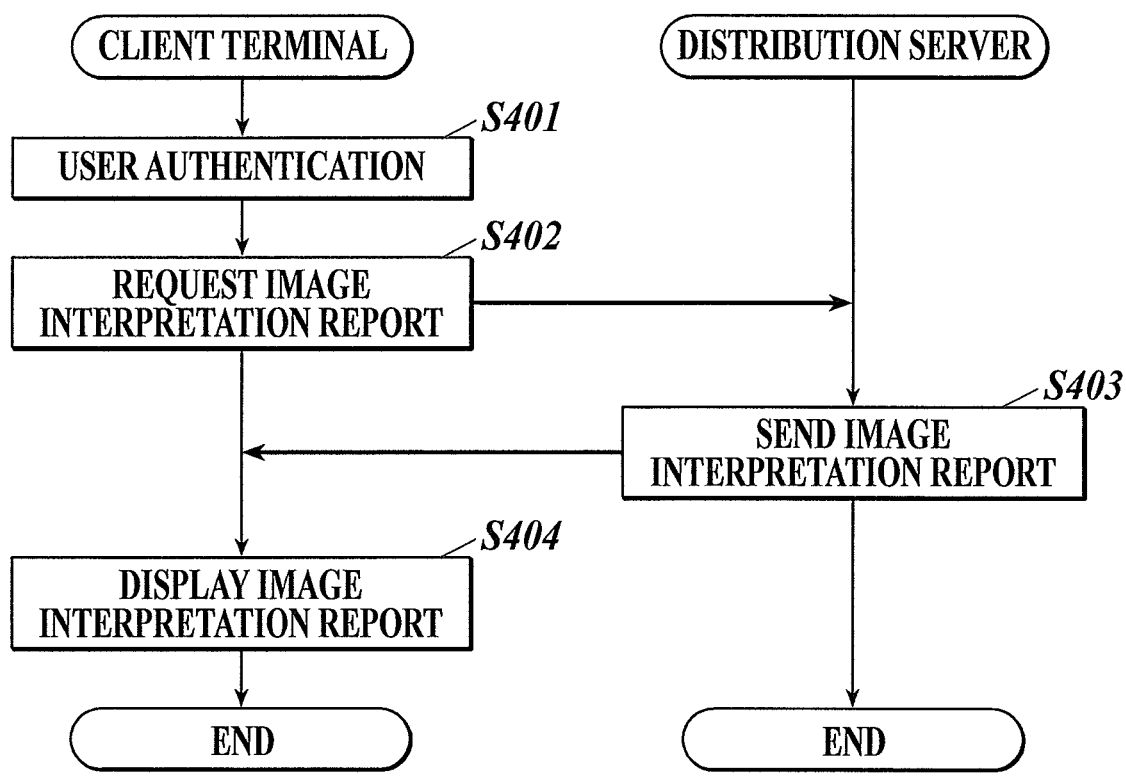
FIG. 9 is a flowchart showing an image interpretation report reference process.

FIG. 9 is a flowchart showing an image interpretation report reference process performed by the client terminal 10 and the distribution server 20.

First, a user of the client terminal 10 in the medical facility 1 is subjected to user authentication (Step S401).

After being authenticated by the distribution server 20, the user of the client terminal 10 requests an image interpretation report from the distribution server 20 (Step S402). Specifically, the user of the client terminal 10 sends a request for an image interpretation report to the distribution server 20 via the communication unit 13 by manipulating a screen displayed on the display 15 with the operation unit 14.

When receiving the request for the image interpretation report and determining that the requested report is stored as the image interpretation report information 242, the distribution server 20 sends the image interpretation report to the client terminal 10 via the communication unit 23 (Step S403).

When receiving the image interpretation report via the communication unit 13, the client terminal 10 displays the image interpretation report on the display 15 (Step S404). Referring to the image interpretation report, the user of the client terminal 10 examines the patient, makes a treatment plan, and provides medical measures, such as treatments and prescriptions, to the patient.

After the image interpretation report reference process, the user of the client terminal 10 evaluates the image interpretation report at his/her convenience through the evaluation input process shown in FIG. 5, and thereby evaluates the image interpretation facility 3 and/or the image interpretation doctor. The image interpretation report reference process and the evaluation input process may be performed successively.

[Image Interpretation Report Quality Management Process]

Next, operation of the remote image interpretation system 100 in an image interpretation report quality management process is described. This process is performed after the distribution server 20 receives an image interpretation report(s).

Figure 10:
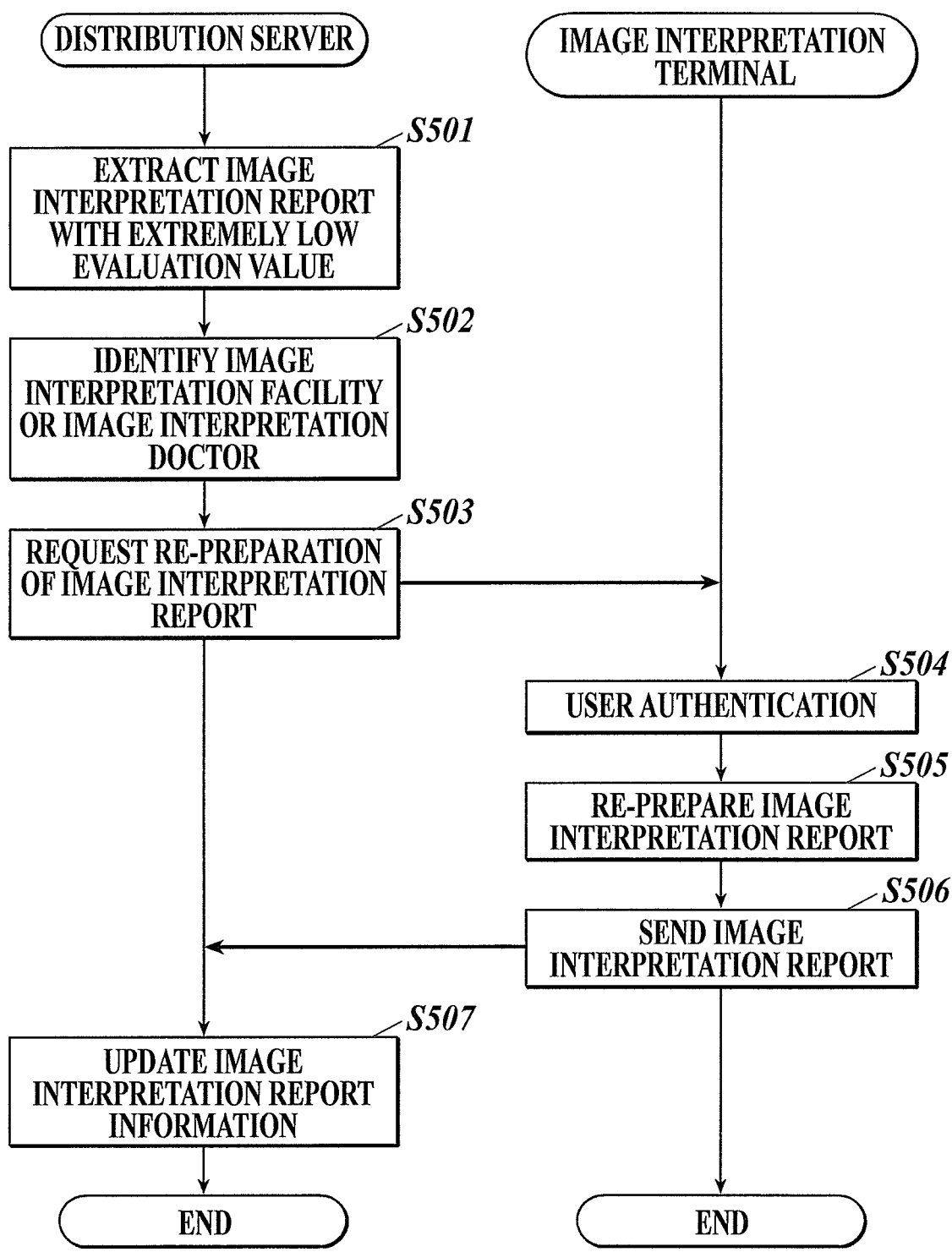
FIG. 10 is a flowchart showing an image interpretation report quality management process.

FIG. 10 is a flowchart showing the image interpretation report quality management process performed by the distribution server 20 and the image interpretation terminal(s) 30.

First, the controller 21 of the distribution server 20 extracts an image interpretation report(s) given an extremely low evaluation value(s) by a user(s) of the client terminal(s) 10 from the image interpretation reports stored as the image interpretation report information 242 (Step S501). It is highly probable that an image interpretation report having an extremely low evaluation value compared to evaluation values given to other image interpretation reports prepared by the same image interpretation facility 3 or image interpretation doctor has a low quality. In order to improve the quality of image interpretation reports, image interpretation reports assumed to be of low quality are identified.

As a method for extracting image interpretation reports assumed to be of low quality, for example, the Smirnov-Grubbs' test or the Thompson's rejection test may be carried out on the assumption that evaluation values given to image interpretation reports prepared by an image interpretation facility 3 or an image interpretation doctor follow a normal distribution.

Next, the controller 21 of the distribution server 20 identifies an image interpretation facility 3 or an image interpretation doctor that has prepared the extracted image interpretation report (Step S502), and sends, to the image interpretation facility 3 or the image interpretation doctor, a request for re-preparation of the image interpretation report via the communication unit 23 (Step S503).

A/The user of the image interpretation terminal 30 is subjected to user authentication (Step S504). When confirming receipt of the request for re-preparation of the image interpretation report to the user of the image interpretation terminal 30, the user thereof re-prepares the image interpretation report (Step S505), and sends the report to the distribution server 20 via the communication unit 33 (Step S506).

When receiving the re-prepared image interpretation report, the distribution server 20 attaches a preparer identifying number to the image interpretation report, and updates the image interpretation report information 242 stored in the storage 24 therewith (Step S507). Then, the image interpretation report quality management process ends. The re-prepared image interpretation report will be sent to the client terminal 10 as desired.

As described above, in the remote image interpretation system 100 according to this embodiment, the process for storing evaluation value information and the process for performing calculation based on evaluation results (evaluation results-based calculation process) are separate and independent processes. Specifically, the distribution server 20 in the intermediary facility 2 stores evaluation value information about quality of image interpretation reports by evaluator and by image interpretation facility 3 and/or image interpretation doctor in the storage 24, whereas in the evaluation results-based calculation process, the distribution server 20 obtains only evaluation values of evaluators who have evaluated a predetermined number of image interpretation reports or more, referring to the evaluation value information stored in the storage 24. That is, only the evaluators who have done many evaluations and are thereby assumed to have a stable evaluation standard are adopted for the evaluation results-based calculation process.

Furthermore, after calculating the statistics and normalizing the evaluation values with the statistics for each of the evaluators, the distribution server 20 calculates, using the normalized evaluation values (evaluation deviation values) of the respective evaluators, the mean evaluation value based on the evaluation deviation values for each image interpretation facility 3 or each image interpretation doctor. This makes it possible to reduce variation in the evaluation standard between evaluators and arbitrarily-manipulated evaluation results as much as possible, and obtain the mean evaluation value.

Furthermore, in the remote image interpretation system 100 according to this embodiment, the distribution server 20 weights the normalized evaluation values (evaluation deviation values) of a predetermined evaluator(s) among the evaluators, and calculates the mean evaluation value. This enables evaluation values of an evaluator(s) to be strongly reflected in the mean evaluation value when it is clear that the evaluator is highly reliable, and thereby makes the mean evaluation value more highly reliable.

Furthermore, in the remote image interpretation system 100 according to this embodiment, the distribution server 20 identifies (extracts) an image interpretation report(s) having an extremely low evaluation value. This enables the intermediary facility 2, for example, to request an image interpretation facility 3 or an image interpretation doctor that has prepared the image interpretation report to re-prepare the report, and thereby contributes to the improvement of the quality of image interpretation reports.

Furthermore, although in the abovementioned embodiment, the user of the client terminal 10 evaluates, as an example, both the image interpretation facility 3 and the image interpretation doctor, the user may evaluate only either of them. Even if the user evaluates only the image interpretation facility 3, the image interpretation doctor who has prepared the image interpretation report can be identified from the image interpretation facility 3, and the evaluation can be associated with the image interpretation doctor.

Other Embodiments

Although one or more embodiments of the present invention have been described in detail, detailed configurations and detailed operations of the apparatuses constituting the remote image interpretation system 100 can be appropriately modified without departing from the scope of the present invention.

Furthermore, in the above description, although an HDD and a nonvolatile semiconductor memory are disclosed as examples of a computer readable storage medium storing the programs of the present invention, the computer readable storage medium is not limited to these. As the computer readable storage medium, a portable storage medium, such as a CD-ROM, may be used. Also, as a medium that provides data of the programs of the present invention via a communication line, a carrier wave can be used.

Although embodiments of the present invention have been described and illustrated in detail, the disclosed embodiments are made for purposes of illustration and examples only and not limitation. The scope of the present invention should be interpreted by terms of the appended claims.

The entire disclosure of Japanese Patent Application No. 2018-106575 filed on Jun. 4, 2018 is incorporated herein by reference in its entirety.

What is claimed is:

1. A remote image interpretation management apparatus having access to a storage storing evaluation values relating to quality of image interpretation reports, the stored evaluation values being accessible on the basis of an evaluator who provided each evaluation value and of the image interpretation facility and/or image interpretation doctor associated with that evaluation value, comprising a hardware processor configured to:
   obtain, from the storage, only evaluation values of evaluators who have evaluated at least a predetermined number of image interpretation reports;
   based on the obtained evaluation values of the evaluators, calculate for each of the evaluators, a statistic of the evaluation values of that evaluator and normalize the evaluation values with the calculated statistic, so as to obtain normalized evaluation values for the respective evaluators; and
   calculate, for each image interpretation facility or each image interpretation doctor, a mean value based on the normalized evaluation values of the respective evaluators.

2. The remote image interpretation management apparatus according to claim 1, wherein the hardware processor is further configured to weight the normalized evaluation values of a predetermined evaluator among the evaluators, and calculate the mean value using this weighting.

3. The remote image interpretation management apparatus according to claim 1, wherein the hardware processor is further configured to:
   extract, from the evaluation values, an evaluation value deviating a predetermined value or more from the calculated mean value; and
   identify an image interpretation doctor that has prepared an image interpretation report having the extracted evaluation value.

4. The remote image interpretation management apparatus according to claim 1, wherein the hardware processor is configured so as to exclude evaluations made by any evaluator having the number of evaluation times less than the predetermined number of times.

5. A remote image interpretation system comprising:
   a client terminal configured to make a request for interpretation of a medical image;
   an image interpretation terminal configured to interpret a medical image; and
   a remote image interpretation management apparatus having access to a storage storing evaluation values relating to quality of image interpretation reports, the stored evaluation values being accessible on the basis of an evaluator who provided each evaluation value and of the image interpretation facility and/or image interpretation doctor associated with that evaluation value, the remote image interpretation management apparatus being configured to relay the request made by the client terminal to the image interpretation terminal, wherein the remote image interpretation management apparatus includes a hardware processor configured to:
   obtain, from the storage, only evaluation values of evaluators who have evaluated at least a predetermined number of image interpretation reports;
   based on the obtained evaluation values of the evaluators, calculate for each of the evaluators, a statistic of the evaluation values of that evaluator and normalize the evaluation values with the calculated statistic, so as to obtain normalized evaluation values for the respective evaluators; and
   calculate, for each image interpretation facility or each image interpretation doctor, a mean value based on the normalized evaluation values of the respective evaluators.

6. A non-transitory computer readable storage medium storing a program to cause a computer of a remote image interpretation management apparatus which relays a request for image interpretation made by a medical facility to an image interpretation facility, and which has access to a storage storing evaluation values relating to quality of image interpretation reports, the stored evaluation values being accessible on the basis of an evaluator who provided each evaluation value and of the image interpretation facility and/or image interpretation doctor associated with that evaluation value, to:
   obtain, from the storage, only evaluation values of evaluators who have evaluated at least a predetermined number of image interpretation reports;
   based on the obtained evaluation values of the evaluators, calculate for each of the evaluators, a statistic of the evaluation values of that evaluator and normalize the evaluation values with the calculated statistic, so as to obtain normalized evaluation values for the respective evaluators; and
   calculate, for each image interpretation facility or each image interpretation doctor, a mean value based on the normalized evaluation values of the respective evaluators.

* * * * *